US006146771A

United States Patent [19]

Wirt et al.

[11] Patent Number: 6,146,771

[45] Date of Patent: Nov. 14, 2000

[54] PROCESS FOR MODIFYING SURFACES USING THE REACTION PRODUCT OF A WATER-INSOLUBLE POLYMER AND A POLYALKYLENE IMINE

[75] Inventors: David F. Wirt, Prescott, Wis.; Larry M. Sirvio, Cottage Grove, Minn.

[73] Assignee: Terumo Cardiovascular Systems Corporation, Somerset, N.J.

[21] Appl. No.: 08/886,720

[22] Filed: Jul. 1, 1997

[51] Int. Cl.[7] .......................... A61L 27/00; A61L 29/00; A61L 31/00; A61L 33/00

[52] U.S. Cl. .......................... 428/515; 424/423; 424/424; 424/487; 424/78.17; 427/2.1; 427/2.28; 427/2.3; 525/54.1

[58] Field of Search .......................... 427/2.1, 2.28, 427/2.3; 424/423, 424, 487, 78.17, 70.17, 70.16; 604/269; 428/515; 523/103, 112, 113, 122; 536/18.7, 20, 21; 525/54.1

[56] References Cited

U.S. PATENT DOCUMENTS

| | | | |
|---|---|---|---|
| 2,016,962 | 10/1935 | Flint et al. | 260/127 |
| 2,918,462 | 12/1959 | Druey et al. | 260/211 |
| 2,954,358 | 9/1960 | Hurwitz . | |
| 3,096,602 | 7/1963 | Newmaker, Jr. | 53/22 |
| 3,325,346 | 6/1967 | Osborg . | |
| 3,453,194 | 7/1969 | Bennett et al. | 284/159.12 |
| 3,475,358 | 10/1969 | Bixler et al. | 260/17.4 |
| 3,616,935 | 11/1971 | Love et al. | 210/500 |
| 3,617,344 | 11/1971 | Leininger et al. | 117/47 |
| 3,634,123 | 1/1972 | Eriksson et al. | 117/47 |
| 3,639,141 | 2/1972 | Dyck | 117/47 |
| 3,673,612 | 7/1972 | Merrill et al. | 3/1 |
| 3,702,348 | 11/1972 | Merlino et al. . | |
| 3,755,218 | 8/1973 | Yen et al. | 260/9 |
| 3,766,104 | 10/1973 | Bonin et al. | 260/9 |
| 3,786,113 | 1/1974 | Vassileff . | |
| 3,796,634 | 3/1974 | Haynes et al. | 195/63 |
| 3,810,781 | 5/1974 | Eriksson et al. | 117/47 |
| 3,826,678 | 7/1974 | Hoffman et al. | 117/81 |
| 3,846,353 | 11/1974 | Grotta | 260/9 |
| 3,853,804 | 12/1974 | Yen et al. | 260/32.6 |
| 3,947,352 | 3/1976 | Cuatrecasas et al. | 210/31 |
| 4,001,583 | 1/1977 | Barrett | 250/303 |
| 4,046,725 | 9/1977 | Pusineri | 260/9 |
| 4,048,064 | 9/1977 | Clark, III | 210/23 |
| 4,085,019 | 4/1978 | Green | 204/159.23 |
| 4,102,746 | 7/1978 | Goldberg | 195/63 |
| 4,116,898 | 9/1978 | Dudley et al. | 260/17.4 |
| 4,118,485 | 10/1978 | Eriksson et al. | 424/183 |
| 4,141,857 | 2/1979 | Levy et al. | 502/439 |
| 4,166,152 | 8/1979 | Baker et al. | 428/522 |
| 4,192,727 | 3/1980 | Ward | 204/159.2 |
| 4,217,338 | 8/1980 | Quash | 424/1 |
| 4,229,838 | 10/1980 | Mano | 3/1.4 |
| 4,239,664 | 12/1980 | Teng et al. | 260/17.4 |
| 4,265,827 | 5/1981 | Sabacky | 260/440 |
| 4,265,927 | 5/1981 | Ericksson et al. | 427/2 |
| 4,268,423 | 5/1981 | Rohrbach et al. | 252/430 |
| 4,272,518 | 6/1981 | Moro et al. | 424/81 |
| 4,273,833 | 6/1981 | De Long | 427/393.5 |
| 4,273,873 | 6/1981 | Sugitachi et al. | 435/180 |
| 4,278,651 | 7/1981 | Hales | 424/1 |
| 4,301,067 | 11/1981 | Koshugi | 260/112.5 |
| 4,326,532 | 4/1982 | Hammar | 128/349 |
| 4,329,383 | 5/1982 | Joh | 428/36 |
| 4,331,697 | 5/1982 | Kudo et al. | 427/2 |
| 4,349,467 | 9/1982 | Williams et al. | 525/54.2 |
| 4,350,806 | 9/1982 | Wagener | 528/289 |
| 4,369,256 | 1/1983 | Casu et al. | 521/25 |
| 4,423,099 | 12/1983 | Mueller et al. | 428/35 |
| 4,424,346 | 1/1984 | Hall et al. | 536/20 |
| 4,521,564 | 6/1985 | Solomon et al. | 525/54.1 |
| 4,526,714 | 7/1985 | Feijen et al. | 260/112 |
| 4,565,740 | 1/1986 | Golander et al. | 428/409 |
| 4,600,652 | 7/1986 | Solomon et al. | 428/423.3 |
| 4,613,517 | 9/1986 | Williams et al. | 427/2 |
| 4,613,665 | 9/1986 | Larm | 536/20 |
| 4,642,242 | 2/1987 | Solomon et al. | 427/2 |
| 4,708,981 | 11/1987 | Zupancic et al. | 525/59 |
| 4,720,512 | 1/1988 | Hu et al. | 523/112 |
| 4,737,544 | 4/1988 | McCain et al. | 525/54.1 |
| 4,786,556 | 11/1988 | Hu et al. | 428/412 |
| 4,800,016 | 1/1989 | Yang | 210/206 |
| 4,806,595 | 2/1989 | Noishiki et al. | 525/54.2 |
| 4,810,784 | 3/1989 | Larm | 536/20 |

(List continued on next page.)

FOREIGN PATENT DOCUMENTS

| | | |
|---|---|---|
| 1160548 | 1/1984 | Canada . |
| 295905B1 | 12/1988 | European Pat. Off. . |
| 0351314 | 1/1990 | European Pat. Off. . |
| 0466178A1 | 1/1992 | European Pat. Off. . |
| 0693293 | 1/1996 | European Pat. Off. . |
| 276814A1 | 3/1990 | Germany . |
| 2 041 377 | 1/1980 | United Kingdom . |
| 88/02623 | 4/1988 | WIPO . |
| 91/16932 | 11/1991 | WIPO . |
| 92/00747 | 1/1992 | WIPO . |
| 92/07023 | 4/1992 | WIPO . |
| 93/02777 | 2/1993 | WIPO . |
| WO93/05793 | 4/1993 | WIPO . |
| WO93/05825 | 4/1993 | WIPO . |
| WO93/10899 | 6/1993 | WIPO . |
| WO96/18423 | 6/1996 | WIPO . |
| WO96/35954A | 11/1996 | WIPO . |
| WO97/07834 | 3/1997 | WIPO . |
| WO 9746590 | 12/1997 | WIPO . |

OTHER PUBLICATIONS

Bruil, "Poly(ethyleneimine) modified filters for the removal of lukocytes from blood", *J. Bio Mat. res.*, 27:1253–68 (1993).

(List continued on next page.)

*Primary Examiner*—Diana Dudash
*Attorney, Agent, or Firm*—Burns, Doane, Swecker & Mathis, LLP

[57] ABSTRACT

A process for modifying a surface of an article that includes treating a surface with a solution that includes an organic solvent, and the reaction product of a substantially water insoluble polymer and a polyalkylene imine to form a modified surface.

35 Claims, No Drawings

U.S. PATENT DOCUMENTS

| | | | |
|---|---|---|---|
| 4,863,611 | 9/1989 | Bernstein et al. | 210/661 |
| 4,865,870 | 9/1989 | Hu et al. | 427/2 |
| 4,871,357 | 10/1989 | Hsu et al. | 604/266 |
| 4,876,126 | 10/1989 | Takemura et al. | 428/35.7 |
| 4,877,680 | 10/1989 | Sakaki et al. | 428/332 |
| 4,935,204 | 6/1990 | Seidel et al. | 424/101 |
| 4,944,767 | 7/1990 | Barbucci et al. | 623/66 |
| 4,987,181 | 1/1991 | Bichon et al. | 525/54.1 |
| 4,996,150 | 2/1991 | Joung et al. | 435/161 |
| 5,000,854 | 3/1991 | Yang | 210/638 |
| 5,013,717 | 5/1991 | Soomon et al. | 514/56 |
| 5,047,020 | 9/1991 | Hsu | 604/266 |
| 5,049,403 | 9/1991 | Larm et al. | 427/2 |
| 5,053,048 | 10/1991 | Pinchuk | 623/1 |
| 5,061,750 | 10/1991 | Feijen et al. | 525/54.1 |
| 5,069,945 | 12/1991 | Wrasidlo | 427/245 |
| 5,087,671 | 2/1992 | Loeppky et al. | 525/328.2 |
| 5,116,962 | 5/1992 | Stüber et al. | 525/54.2 |
| 5,132,108 | 7/1992 | Narayanan et al. | 424/78.17 |
| 5,145,956 | 9/1992 | Lam et al. | 536/124 |
| 5,151,192 | 9/1992 | Matkovich et al. | 210/646 |
| 5,159,050 | 10/1992 | Onwumere | 528/67 |
| 5,165,919 | 11/1992 | Sasaki et al. | 424/488 |
| 5,182,317 | 1/1993 | Winters et al. | 523/112 |
| 5,198,493 | 3/1993 | Holmberg et al. | 525/54.1 |
| 5,211,850 | 5/1993 | Shettigar et al. | 210/645 |
| 5,212,008 | 5/1993 | Malhotra et al. | 428/216 |
| 5,213,898 | 5/1993 | Larm et al. | 428/422 |
| 5,217,492 | 6/1993 | Guire et al. | 623/11 |
| 5,219,926 | 6/1993 | Lindman et al. | 525/54.1 |
| 5,240,994 | 8/1993 | Brink et al. | 525/54.2 |
| 5,250,613 | 10/1993 | Bergstrom et al. | 525/54.1 |
| 5,258,041 | 11/1993 | Guire et al. | 623/66 |
| 5,308,641 | 5/1994 | Cahalan et al. | 427/2 |
| 5,350,800 | 9/1994 | Verhoeven et al. | 525/54.2 |
| 5,391,580 | 2/1995 | Douglas et al. | 521/27 |
| 5,415,938 | 5/1995 | Cahalan et al. | 428/409 |
| 5,416,198 | 5/1995 | Anderson et al. | 536/111 |
| 5,476,715 | 12/1995 | Otto | 428/407 |
| 5,532,311 | 7/1996 | Sirvio et al. | 525/54.2 |
| 5,563,056 | 10/1996 | Swan et al. | 435/180 |
| 5,576,072 | 11/1996 | Hostettler et al. | 427/388.4 |
| 5,607,475 | 3/1997 | Cahalan et al. | 623/11 |
| 5,614,310 | 3/1997 | Delgado et al. | 428/316.6 |
| 5,658,561 | 8/1997 | Nakabayashi et al. | 424/78.37 |
| 5,662,985 | 9/1997 | Jensen et al. | 428/195 |
| 5,672,638 | 9/1997 | Verhoeven et al. | 427/2.25 |
| 5,688,855 | 11/1997 | Stoy et al. | 524/505 |
| 5,700,395 | 12/1997 | Thetford et al. | 252/309 |
| 5,700,848 | 12/1997 | Soon-Shiong et al. | 522/7 |
| 5,702,754 | 12/1997 | Zhong | 427/2.28 |
| 5,766,478 | 6/1998 | Smith et al. | 210/638 |
| 5,811,151 | 9/1998 | Hendriks et al. | 427/333 |
| 5,837,377 | 11/1998 | Sheu et al. | 428/412 |
| 5,906,734 | 5/1999 | Girot et al. | 210/198.2 |

OTHER PUBLICATIONS

Hou et al., "A Method for Extracorporeal Heparin Removal from Blood by Affinity Chromatography", *Artifical Organs*, 14(6):436–442 (1990).

Hoffman et al., "A New Method for Covalent Coupling of Heparin and Other Glycosaminoglycans to Substances Containing Primary Amino Groups", *Carbohydrate Research*, 117 (1983) p. 328–331.

Klein, "A Hollow Fiber Device for Direct Absorption of Heparin From Whole Blood", *JASN* 7:9 p. 1410 (1996).

Larm et al., "An Approach to Antithrombois by Surface Modification", *Progress in Artifical Organs*, p. 313–318 (1985).

Larm et al., "A New Non–Thrombogenic Surface Prepared by Selective Covalent Binding of Heparin Via A Modified Reducing Terminal Residue", (1984).

Ma et al., "Interaction of Heparin with Polyallylamine–Immobilized Surfaces," *J. Biom. Mat. Res.*, 27:357–365 (1993).

Marchisio et al., "Novel Approach To The Problems of Heparin In Hemodialysis: The Use of A Deheparinizing Filter, " *Polymers In Med. III*, p. 111–117 and 120 (1988) (pp. 118 and 119 missing).

Matthey et al., "A Selective De–Heparinizer Filter Made of New Cross–Linked Polymers of a Poly–Amido–Amine Structure," *Experientia*, 29: 93–95 (1973).

Wenz et al., "Rapid Removal of Heparin from Plasma by Affinity Filtration," *Coagulation and Transf. Med.*, 96:3, p. 385–390 (1991).

Tao et al., "Extracorporeal Heparin Removal Following Cardiopulmonary Bypass with a Heparin Removal Device: An Alternative to Protamine," *Crit. Care Med.*, 25:1 (Suppl.) (1997).

PROCESS FOR MODIFYING SURFACES USING THE REACTION PRODUCT OF A WATER-INSOLUBLE POLYMER AND A POLYALKYLENE IMINE

BACKGROUND OF THE INVENTION

The invention relates to modifying the surface of an article.

Surfaces of, e.g., medical devices must often be modified. For example, the surfaces of medical devices that are in direct contact with blood or blood products (e.g., blood oxygenators, blood pumps, catheters, and tubing) have been treated with biologically active agents such as heparin or derivatives thereof to make such surfaces nonthrombogenic in an effort to prevent clotting or clot formation related to surface contact with blood or blood products.

SUMMARY OF THE INVENTION

In one aspect, the invention features a process for modifying the surface of an article that includes treating the surface with a solution that includes (a) an organic solvent, and (b) the reaction product of a substantially water insoluble polymer and a polyalkylene imine (e.g., polyethylene imine) to form a modified surface.

In one preferred embodiment, the treated surface may be reacted further with a biologically active agent. The biologically active agent may include negatively charged materials. Specific examples of biologically active agents include anti-thrombotic agents (e.g., a glycosaminoglycan (or a derivative thereof) such as heparin or a heparin derivative). Other examples of suitable biologically active agents include heparan sulfate, hyaluronic acid, dermatan sulfate, chitosan, derivatives thereof, and combinations thereof.

Preferred substantially water-insoluble polymers include functional groups such as ester groups that are capable of forming a covalent bond with the polyalkylene imine. Specific examples include the reaction product of an alkyl acrylate and an alkyl methacrylate (e.g., isooctyl acrylate and methyl methacrylate); the reaction product of an alkyl methacrylate, an alkylacrylate, and N-vinyl pyrrolidone (e.g., methyl methacrylate, isooctyl acrylate, and N-vinyl pyrrolidone); and the reaction product of an alkyl acrylate, an alkyl methacrylate, and a hydroxyalkyl methacrylate (e.g., isooctyl acrylate, methyl methacrylate, and hydroxypropyl methacrylate). The acrylate, methacrylate, and N-vinyl pyrrolidone may be provided in the form of monomers, oligomers, or a combination thereof.

The invention also features an article that includes a substrate having a modified surface that includes the reaction product of a substantially water insoluble polymer and a polyalkylene imine. The article may further include a biologically active agent bound to the surface.

Throughout this application the following definitions apply:

A "biologically active agent" is a material which, when in contact with a patient's blood, plasma, or other body fluids or tissues under physiological conditions, exhibits biological activity. For instance, a material such as heparin is "biologically active" in the sense that it acts as an anti-coagulant in the presence of blood.

The invention provides a simple and effective means for modifying the surface of an article, e.g., such that when in contact with a patient's blood, plasma, or other body fluids, the surface does not cause an adverse physiological reaction.

Other features and advantages of the invention will be apparent from the following description of the preferred embodiments thereof, and from the claims.

DESCRIPTION OF THE PREFERRED EMBODIMENTS

The present invention provides a process for producing modified surfaces (e.g., the surfaces of medical devices such as filters, membranes, tubes, catheters, oxygenator, intravascular probes, blood pumps, blood gas sensing devices, and the like). The surface may be a polymer, ceramic, or metal surface. Examples of suitable polymer surfaces include polypropylene, poly (vinyl chloride), poly (methyl methacrylate), polytetrafluoroethylene, polysulfone, silicone rubber, poly (ethylene terephthalate), polycarbonate, polyethylene, polystyrene, and polyurethane.

In general, the surface is contacted with a priming solution that contains an organic solvent and the reaction product of a polyalkylene imine, such as polyethylene imine, and a substantially water insoluble polymer, and then dried. The resulting primed surface is capable of binding with a biologically active agent. Although the system is designed to be functional after a single coating step, the solution may be coated on the surface and dried as many times as is necessary to achieve the desired concentration of functional groups on the surface. The particular amount of coating and concentration of functional groups on the surface will depend upon the particular application for which the treated surface is intended.

The surface may then be contacted with a biologically active agent to bind the biologically active agent to the primed surface. The biologically active agent may be an anti-thrombotic agent (e.g., a glycosaminoglycan (or derivative thereof) such as heparin or a heparin derivative), an anti-microbial agent, a therapeutic agent (e.g., a drug or growth factor), an enzyme, or a cell attachment protein. Other examples of suitable biologically active agents include heparin, heparan sulfate, hyaluronic acid, dermatan sulfate, chitosan, and derivatives thereof. The agents may be used alone or in combination with each other.

Binding may be either ionic or covalent, with covalent being preferred. In the case of ionic binding, it is preferred that the biologically active agent include one or more negatively charged groups. Following addition of the biologically active agent, the biologically active agent may then be treated with a crosslinking agent, if desired.

In the case of covalent binding, it is preferred to contact the primed surface with a biologically active agent having free aldehyde groups (generated, e.g., by periodate oxidation) in the presence of a reducing agent such as sodium cyanoborohydride. The covalent binding most likely occurs via formation of a Schiff's base initially, which is then readily reduced to a secondary amine in the presence of the sodium cyanoborohydride.

Covalent binding may also be accomplished using a coupling agent such as a carbodiimide, rather than sodium cyanoborohydride. In this case, the covalent linkage occurs between carboxylate groups on the biologically active agent and amine groups on the primed surface.

Preferred priming solutions include between about 0.1 to about 20% solids in a solution that includes between about 50 and about 99.9% organic solvent and up to about 50% water. The weight to weight ratio of substantially water insoluble polymer to polyethylene imine is preferably between about 0.1:1 and about 10:1, more preferably about 4:1.

Suitable polyalkylene imines are those having an average molecular weight of between about 300 and 1,000,000. One example of a suitable polyalkylene imine is polyethylene imine having an average molecular weight of 750,000, available from the Aldrich Chemical Co., Milwaukee, Wis.

Preferred substantially water insoluble polymers are those polymers that provide functional groups capable of forming a covalent bond with the amine groups of the polyalkylene imine while not interfering with the ability of the polyalkylene imine to bind to a biologically active agent. The polymer preferably is soluble in those organic solvents in which the polyalkylene imine is soluble.

Suitable substantially water insoluble polymers include substantially water insoluble acrylate polymers such as, e.g., alkyl acrylate-alkyl methacrylate copolymers (e.g., copolymers of isooctyl acrylate and methyl methacrylate), alkyl methacrylate-alkyl acrylate-N-vinyl pyrrolidone terpolymers (e.g., methyl methacrylate-isooctyl acrylate-N-vinyl pyrrolidone), and alkyl acrylate-alkyl methacrylate-hydroxyalkyl methacrylate terpolymers (e.g., isooctyl acrylate-methyl methacrylate-hydroxypropyl methacrylate).

Examples of alkyl methacrylate-alkyl acrylate-N-vinyl pyrrolidone terpolymers, and their methods of manufacture, are described in U.S. Pat. No. 4,584,192 (Dell), incorporated herein by reference.

Preferred organic solvents are those capable of dissolving both the substantially water insoluble polymer and polyalkylene imine, and rapidly evaporating after the application of the priming solution to the substrate surface. Suitable organic solvents include tetrahydrofuran and alkyl alcohols such as, e.g., methanol, ethanol, and isopropyl alcohol.

The invention will now be further described by way of the following non-limiting examples.

EXAMPLES

Example 1

Methyl methacrylate monomers, isooctyl acrylate monomers and N-vinyl pyrrolidone monomers were polymerized as described in Examples 2–8, formulation D of U.S. Pat. No. 4,584,192, to form a terpolymer. The terpolymer was then repeatedly washed and distilled so as to remove the acetone. Once the acetone was removed, the terpolymer was placed in isopropyl alcohol.

The terpolymer solution and polyethylene imine were then placed in a solution of isopropyl alcohol and water. The resulting solution contained 4:1 polyethylene imine/terpolymer, 2.5% solids solution in 82.5% isopropyl alcohol and 15% water. The solution was allowed to react for four hours at 50° C., after which it was coated on a piece of woven polyester. After evaporation of the solvent, a portion of the sample was separated and rinsed with water. It was then stained with 8-hydroxy-7-(4-sulfo-1-naphthylazo)-5-quinoline sulfonic acid (SNAZOXS), which revealed the presence of PEI.

The remaining portion of the sample was rinsed with 25% saline solution and then stained with SNAZOXS. Staining also revealed the presence of PEI, demonstrating that the PEI does not rinse off even with saline solution.

Example 2

Two grams (g) of a isooctyl acrylate/methyl methacrylate (IOA/MMA) copolymer, having 55 parts IOA and 45 parts MMA, was dissolved in 35 g of tetrahydrofuran (THF). Two grams of polyethylene imine (PEI) (average molecular weight of 750,000, available from Aldrich Chemical Co., Milwaukee, Wis.) was added to the IOA/MMA THF solution and the mixture was allowed to react for four hours at 50° C. The solution was coated on a piece of woven polyester. After evaporation of the solvent, the polyester sample was rinsed with a 25% saline solution. The polyester sample was then stained with 8-hydroxy-7-(4-sulfo-1-naphthylazo)-5-quinoline sulfonic acid (SNAZOXS), which revealed the presence of PEI.

Example 3

Two grams of IOA/MMA/hydroxypropyl methacrylate (HPMA) terpolymer, having 50 parts IOA, 40 parts MMA and 10 parts HPMA, was dissolved in 35 g of THF. Two grams of PEI was added to the IOA/MMA/HPMA THF solution and the mixture was allowed to react for four hours at 50° C. The solution was coated on a piece of woven polyester. After evaporation of the solvent, the polyester sample was rinsed with a 25% saline solution. The polyester sample was then stained with SNAZOXS, which revealed the presence of PEI.

Example 4

An isooctyl acrylate-methyl methacrylate-N-vinyl pyrrolidone terpolymer was prepared following the procedure of Example 1 except that a polycarbonate sample was dip coated in the solution and allowed to dry. Next, the dried sample was rinsed thoroughly with water, after which heparin was attached to the primed polycarbonate surface by immersing the sample in a citrate-buffered saline solution containing 0.04% periodate oxidized heparin and 0.004% sodium cyanoborohydride (pH=3.9) for a period of 30 minutes at 50° C. The heparinized sample was then rinsed for five minutes in 25% saline solution to remove ionically bound heparin, leaving only covalently bound heparin. The sample was subjected to a thrombin inhibition assay following the procedure described in Sirvio et al., U.S. Pat. No. 5,532,311 (hereby incorporated by reference). The results of the assay demonstrated that the activity of heparin on the sample surface corresponded to 0.14 micrograms/$cm^2$.

Other embodiments are within the claims.

What is claimed is:

1. A process for modifying a surface of an article comprising:

forming a solution comprising (a) an organic solvent, and (b) the reaction product of a substantially water insoluble polymer and a polyalkylene imine; and forming a coating on the surface of the article with the solution to form a modified surface.

2. The process of claim 1, further comprising contacting said modified surface with a biologically active agent to bind said biologically active agent to said surface.

3. The process of claim 2, wherein said biologically active agent comprises a negatively charged material.

4. The process of claim 2, wherein said biologically active agent comprises an anti-thrombotic agent.

5. The process of claim 2, wherein said biologically active agent comprises a glycosaminoglycan.

6. The process of claim 2, wherein said biologically active agent comprises heparin.

7. The process of claim 2, wherein said biologically active agent is selected from the group consisting of heparan sulfate, hyaluronic acid, dermatan sulfate, chitosan, and combinations thereof.

8. The process of claim 1, wherein said substantially water insoluble polymer comprises functional groups capable of forming a covalent bond with said polyalkylene imine.

9. The process of claim 1, wherein said substantially water insoluble polymer comprises ester groups.

10. The process of claim 1, wherein said substantially water insoluble polymer comprises the reaction product of an alkyl acrylate and an alkyl methacrylate.

11. A process for modifying a surface of an article comprising:

treating a surface with a solution comprising a) an organic solvent, and (b) the reaction product of a substantially water insoluble polymer and a polyalkylene imine to form a modified surface, wherein said substantially water insoluble polymer comprises the reaction product of isooctyl acrylate and methyl methacrylate.

12. A process for modifying a surface of an article comprising:

treating a surface with a solution comprising (a) an organic solvent, and (b) the reaction product of a substantially water insoluble polymer and a polyalkylene imine to form a modified surface, wherein said substantially water insoluble polymer comprises the reaction product of an alkyl methacrylate, an alkyl acrylate, and N-vinyl pyrrolidone.

13. The process of claim 12, wherein said substantially water insoluble polymer comprises the reaction product of methyl methacrylate, isooctyl acrylate, and N-vinyl pyrrolidone.

14. A process for modifying a surface of an article comprising:

treating a surface with a solution comprising (a) an organic solvent, and (b) the reaction product of a substantially water insoluble polymer and a polyalkylene imine to form a modified surface, wherein said substantially water insoluble polymer comprises the reaction product of an alkyl acrylate, an alkyl methacrylate, and a hydroxy alkyl methacrylate.

15. The process of claim 14, wherein said substantially water insoluble polymer comprises the reaction product of isooctyl acrylate, methyl methacrylate, and hydroxypropyl methacrylate.

16. The process of claim 1, wherein said polyalkylene imine comprises polyethylene imine.

17. An article comprising a substrate having a modified surface comprising the reaction product of a substantially water insoluble polymer and a polyalkylene imine, wherein the article is prepared by the process of claim 1.

18. The article of claim 17, wherein said polyalkylene imine comprises polyethylene imine.

19. The article of claim 17, further comprising a biologically active agent bound to said surface.

20. The article of claim 19, wherein said biologically active agent comprises a negatively charged material.

21. The article of claim 19, wherein said biologically active agent comprises an anti-thrombotic agent.

22. The article of claim 19, wherein said biologically active agent comprises a glycosaminoglycan.

23. The article of claim 19, wherein said biologically active agent comprises heparin.

24. The article of claim 19, wherein said biologically active agent is selected from the group consisting of heparan sulfate, hyaluronic acid, dermatan sulfate, chitosan, and combinations thereof.

25. The article of claim 17, wherein said substantially water insoluble polymer comprises functional groups capable of forming a covalent bond with said polyalkylene imine.

26. The article of claim 17, wherein said substantially water insoluble polymer comprises ester groups.

27. The article of claim 17, wherein said substantially water insoluble polymer comprises the reaction product of an alkyl acrylate and an alkyl methacrylate.

28. An article comprising a substrate having a modified surface comprising the reaction product of a substantially water insoluble polymer and a polyalkylene imine, wherein said substantially water insoluble polymer comprises the reaction product of isooctyl acrylate and methyl methacrylate.

29. An article comprising a substrate having a modified surface comprising the reaction product of a substantially water insoluble polymer and a polyalkylene imine, wherein said substantially water insoluble polymer comprises the reaction product of an alkyl methacrylate, an alkyl acrylate, and N-vinyl pyrrolidone.

30. The article of claim 29, wherein said substantially water insoluble polymer comprises the reaction product of methyl methacrylate, isooctyl acrylate, and N-vinyl pyrrolidone.

31. An article comprising a substrate having a modified surface comprising the reaction product of a substantially water insoluble polymer and a polyalkylene imine, wherein said substantially water insoluble polymer comprises the reaction product of an alkyl acrylate, an alkyl methacrylate, and a hydroxy alkyl methacrylate.

32. The article of claim 31, wherein said substantially water insoluble polymer comprises the reaction product of isooctyl acrylate, methyl methacrylate, and hydroxypropyl methacrylate.

33. An article comprising a substrate having a modified surface comprising:

(a) a primer comprising the reaction product of (i) a substantially water insoluble polymer comprising the reaction product of an alkyl acrylate, an alkyl methacrylate, and N-vinyl pyrrolidone and (ii) polyethylene imine; and (b) a biologically active agent comprising heparin covalently bound to said primer, wherein the article is formed by a process comprising forming a solution comprising the reaction product of (i) the substantially water insoluble polymer comprising the reaction product of the alkyl acrylate, the alkyl methacrylate, and the N-vinyl pyrrolidone and (ii) the polyethylene imine; and coating the surface of the article with the solution to form a modified surface.

34. The process of claim 1, wherein the weight ratio of the water insoluble polymer to the polyalkylene imine is 0.1:1 to 10:1.

35. The article of claim 17, wherein the weight ratio of the water insoluble polymer to the polyalkylene imine is 0.1:1 to 10:1.

* * * * *